US010502682B2

(12) United States Patent
Dreyer et al.

(10) Patent No.: US 10,502,682 B2
(45) Date of Patent: Dec. 10, 2019

(54) DEVICE FOR DETERMINING THE CONCENTRATION OF AT LEAST ONE GAS COMPONENT IN A BREATHING GAS MIXTURE

(71) Applicant: Drägerwerk AG & Co. KGaA, Lübeck (DE)

(72) Inventors: Peter Dreyer, Pansdorf (DE); Günter Steinert, Bad Oldesloe (DE); Bernd-Michael Dicks, Damlos (DE); Ralph-Peter Jacobi, Reinbek (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 15/795,954

(22) Filed: Oct. 27, 2017

(65) Prior Publication Data

US 2018/0120224 A1 May 3, 2018

(30) Foreign Application Priority Data

Oct. 28, 2016 (DE) .......................... 10 2016 012 970

(51) Int. Cl.
*G01N 21/35* (2014.01)
*G01J 5/00* (2006.01)
(Continued)

(52) U.S. Cl.
CPC ........... *G01N 21/3504* (2013.01); *A61B 5/08* (2013.01); *G01J 5/0014* (2013.01);
(Continued)

(58) Field of Classification Search
CPC ....... G01N 21/3504; G01N 2001/2244; G01N 2015/0046; G01N 2021/1704;
(Continued)

(56) References Cited

U.S. PATENT DOCUMENTS 5,261,415 A 11/1993 Dussault
5,610,400 A * 3/1997 Weckstrom ........ G01N 21/3504
250/339.13
(Continued)

FOREIGN PATENT DOCUMENTS

DE 296 02 282 U1 6/1996
DE 100 47 728 B4 12/2005
(Continued)

*Primary Examiner* — Taeho Jo
(74) *Attorney, Agent, or Firm* — McGlew and Tuttle, P.C.

(57) ABSTRACT

A device (1) for determining the concentration of a gas component is configured with a radiation source (30) for emitting (31) a light radiation or heat radiation in an infrared wavelength range. A detector array (40) has at least two detector elements (50, 60), configured to detect the radiation generated by the radiation source (30), in an angular arrangement (52, 62) and with filter elements (51, 61). At least one of the two detector elements (50, 60) is oriented in an angular arrangement (52, 62) in relation to a vertical axis (32), so that a range of overlap (65) is obtained due to the angular arrangements (52, 62). The range of overlap (65) causes attenuations in the propagation of light, which attenuations may be due, for example, to gas molecules or moisture (400), affect both detector elements (50, 60) and are thus compensated concerning the concentration determination.

8 Claims, 6 Drawing Sheets

(51) Int. Cl.
*G01N 33/497* (2006.01)
*G01N 21/3504* (2014.01)
*A61B 5/08* (2006.01)
*G01N 21/31* (2006.01)

(52) U.S. Cl.
CPC ... *G01N 33/497* (2013.01); *G01N 2021/3166* (2013.01); *G01N 2021/3177* (2013.01); *G01N 2201/0662* (2013.01); *G01N 2201/0686* (2013.01)

(58) Field of Classification Search
CPC .............. G01N 21/314; G01N 21/783; G01N 2201/068; G01N 1/2205; G01N 21/35; G01N 21/3518; G01N 21/359; G01N 33/497; G01N 2021/3166; G01N 2021/3177; G01N 2201/0662; G01N 2201/0686; A61B 5/08; G01J 5/0014
USPC ....................................................... 250/343
See application file for complete search history.

(56) References Cited

U.S. PATENT DOCUMENTS

| | | | | |
|---|---|---|---|---|
| 5,721,430 | A | 2/1998 | Wong | |
| 6,277,081 | B1* | 8/2001 | Susi | G01N 21/3504 250/345 |
| 6,512,230 | B1* | 1/2003 | von Lerber | G01N 21/3504 250/339.13 |
| 6,955,652 | B1* | 10/2005 | Baum | A61B 5/0813 600/529 |
| 7,564,558 | B2* | 7/2009 | Martin | G01J 3/22 356/246 |
| 9,488,577 | B2* | 11/2016 | Andre | G01N 21/61 |
| 9,549,702 | B1* | 1/2017 | Kerness | A61B 5/4845 |
| 2001/0015408 | A1* | 8/2001 | Stock | G01N 21/314 250/338.5 |
| 2003/0028120 | A1* | 2/2003 | Mault | A61B 5/0833 600/531 |
| 2004/0007667 | A1* | 1/2004 | Diekmann | G01N 21/3504 250/343 |
| 2004/0203169 | A1 | 10/2004 | Dreyer et al. | |
| 2004/0238746 | A1* | 12/2004 | Dreyer | G01N 21/3504 250/345 |
| 2006/0263256 | A1* | 11/2006 | Koshel | C23C 8/06 422/83 |
| 2007/0102639 | A1* | 5/2007 | Cutler | G01N 21/3504 250/339.13 |
| 2007/0259440 | A1* | 11/2007 | Zhou | G01N 21/3504 436/141 |
| 2008/0220535 | A1* | 9/2008 | LeBoeuf | B82Y 30/00 436/164 |
| 2009/0268204 | A1* | 10/2009 | Tkachuk | G01N 21/3504 356/437 |
| 2010/0049017 | A1* | 2/2010 | LeBoeuf | A61B 5/14552 600/310 |
| 2010/0208268 | A1* | 8/2010 | Haveri | G01N 21/05 356/437 |
| 2011/0090505 | A1* | 4/2011 | Kuze | G01N 21/3504 356/437 |
| 2013/0059396 | A1* | 3/2013 | LeBoeuf | B82Y 30/00 436/149 |
| 2013/0221224 | A1* | 8/2013 | Maksyutenko | G01N 21/0303 250/343 |
| 2014/0243630 | A1* | 8/2014 | Melker | A61M 16/0627 600/324 |
| 2015/0096349 | A1* | 4/2015 | Johnson | G01N 1/38 73/23.37 |
| 2015/0192517 | A1* | 7/2015 | Andre | G01N 21/61 250/343 |
| 2015/0241339 | A1* | 8/2015 | Maksyutenko | G01N 21/3504 250/343 |
| 2016/0371590 | A1* | 12/2016 | Blackley | G06N 5/04 |
| 2017/0102322 | A1* | 4/2017 | Goldring | G01N 21/3504 |

FOREIGN PATENT DOCUMENTS

| | | |
|---|---|---|
| EP | 196 993 A2 | 10/1986 |
| EP | 0 536 727 B1 | 12/1994 |
| JP | 2009 128 111 A | 6/2009 |
| JP | 2014509383 A | 4/2014 |
| JP | 2014081261 A | 5/2014 |

* cited by examiner

DEVICE FOR DETERMINING THE CONCENTRATION OF AT LEAST ONE GAS COMPONENT IN A BREATHING GAS MIXTURE

CROSS REFERENCE TO RELATED APPLICATIONS

This application claims the benefit of priority under 35 U.S.C. § 119 of German Application 10 2016 012 970.0, filed Oct. 28, 2016, the entire contents of which are incorporated herein by reference.

FIELD OF THE INVENTION

The present invention pertains to a device for determining the concentration of at least one gas component in a breathing gas mixture.

BACKGROUND OF THE INVENTION

Devices for determining the concentrations of gas components in a breathing gas mixture are used, among other things, to determine concentration values of carbon dioxide exhaled by patients. DE 10047728 B4 describes a sensor for measuring carbon dioxide, laughing gas and anesthetic gases. A detector array comprising four optical filter elements with associated detector elements is shown. The combinations of filter and detector elements are arranged around a beam-mixing system. Such a beam-mixing system, shown in a configuration in a multispectral sensor, is shown in EP 0 536 727 B1. Such a sensor system is used in routine clinical practice, for example, in a capnograph as well as in a so-called CO2 mainstream sensor or also in a $CO_2$ sidestream sensor. U.S. Pat. No. 5,261,415 B2 shows a $CO_2$ mainstream capnography sensor. An insert, in which an infrared optical measuring system is, in turn, arranged, is arranged in a cuvette, which carries the breathing gas. EP 0 536 727 B1 shows the complicated manner in which optical components must be arranged and configured in order to achieve an effective beam mixing. The beam mixing has the task of allowing locally occurring contaminations to become effective symmetrically in both the reference channel and the measuring channel. This is necessary to ensure that the ratio of the measuring channel to the reference channel is guaranteed at all working points such that contaminations, water vapor as well as aging effects of the detector elements can be permanently compensated during the operation. The drawback of the solution is, as is shown in EP 0 536 727 B1, that the beam mixing brings about a signal weakening due to the infrared light having to be deflected and reflected in the measuring cuvette several times. This signal weakening leads to a worse signal-to-noise ratio (SNR). To attain the necessary measured value solution, an increase in the measurement effect must be compensated by means of an increase in the absorption length. An increase in the absorption length results in an enlargement of the physical configuration. The requirement for beam mixing and for the plurality of components involved in it is, furthermore, disadvantageous in terms of the complexity and high tolerance requirements of the components involved (tolerance chain) as well as the high manufacturing costs resulting herefrom for a multispectral sensor of the type proposed in EP 0 536 727 B1.

SUMMARY OF THE INVENTION

Based on the above-described state of the art and the drawbacks described in this connection, the object of the present invention is to provide a device for determining the gas concentration of at least one gas component in a breathing gas mixture, which is characterized by a small space requirement as well as comparatively favorable manufacturing costs.

The following components are provided according to the present invention in the device for determining the concentration of at least one gas component in a breathing gas mixture: —a radiation source suitable and configured to radiate a light radiation or heat radiation in a wavelength range of lambda1 ($\lambda 1$)=3,000 nm to lambda2 ($\lambda 2$)=10,000 nm, —at least two detector elements configured suitably to detect the light radiation or heat radiation generated by the radiation source, —at least two bandpass filter elements arranged at the detector elements, and—a control unit.

The light emitted by the radiation source is emitted with an emission direction essentially at right angles from the emitting surface of the radiation source in the direction of a vertical axis of the device.

The wavelength range of lambda1 ($\lambda 1$)=2.5 µm to lambda2 ($\lambda 2$)=14.0 µm of the radiation source makes possible an infrared optical measurement of laughing gas concentrations, carbon dioxide concentration as well as of various hydrocarbons, for example, volatile anesthetic gases.

The detector elements are configured, for example, as semiconductor detectors, pyroelectric detectors (pyrodetectors), thermoelectric detectors (thermopiles, thermocouples), as heat detectors (bolometers) as well as as combinations of semiconductor detectors and heat detectors. The detector elements are configured for detecting light for an infrared radiation in infrared wavelength ranges, in which absorption by gases, for example, carbon dioxide, typically occurs.

The bandpass filter elements are configured, for example, as optical interference filters in the form of interference layers on a substrate. These transmit light in a defined wavelength range.

The arrangement of the bandpass filter elements is configured such that the infrared radiation emitted by the radiation source passes through the bypass filter elements in front of the detector elements in a direct beam path or also in an indirect beam path, for example, by means of a deflection of the infrared radiation through reflective elements or mirror arrays in the beam path. At least one of the at least two bandpass filter is configured as being optically transparent for an infrared radiation in a wavelength range, which radiation is absorbed by a measured gas.

The detector element, at which this bandpass filter element is arranged, represents the so-called measuring channel in the device for determining the concentration of at least one gas component in a breathing gas mixture.

At least one of the at least two bandpass filter elements is configured as being optically transparent for an infrared radiation in a wavelength range, which radiation is not absorbed or is only slightly absorbed by the measured gas, in a wavelength range.

The detector element, at which this bandpass filter element is arranged, represents a so-called reference channel in the device for determining the concentration of at least gas component in a breathing gas mixture.

Measured gases, often also called target gases, are, for example, carbon monoxide or laughing gas, as well as a plurality of gaseous, organic compounds, such as methane or volatile anesthetic gases, for example, halothane, isoflurane, desflurane, and enflurane.

Measured values of the measuring channel and reference channel are determined by means of the control unit in the device for determining the concentration of at least one gas component in a breathing gas mixture and are related to one another. A quotient of detected measured values of the measuring channel to detected measured values of the reference channel is usually formed, and this quotient indicates an indicator of a concentration of the measured gas in the device for determining the concentration, i.e., the concentration of a quantity of gas, which is present in the beam path.

The arrangement in space of the at least two detector elements and of the bandpass filter elements in relation to the radiation source or in relation to the axis of the radiation is such that at least one of the two detector elements is arranged with at least one of the bandpass filter elements arranged at the at least two detector elements in an angular arrangement with an angle in a range of 5° to 80° to an axis extending through the radiation source parallel to the direction of or identical to the direction of the emission of the radiation source.

The at least two detector elements with the at least two bandpass filter elements arranged thereon now form at least two angular arrangements to the axis extending vertically from the plane of the emission of the radiation source. The at least two angular arrangements with the at least two detector elements and with the bandpass filter elements arranged at the at least two detector elements together form a detector array. The at least two angular arrangements are arranged at an angle to the axis extending vertically from the plane of the emission of the radiation source such that the axis extending vertically from the plane of the emission of the radiation source extends between the at least two angular arrangements.

At least one of the angular arrangements is not arranged and configured in a parallel orientation to the plane of the emission of the radiation source, but is arranged at an angle to the axis extending vertically from the plane of the emission of the radiation source such that the axis extending vertically from the plane of the emission of the radiation source extends between the at least two angular arrangements and at least one of the angular arrangements is sloped at an angle towards the axis extending vertically from the plane of the emission of the radiation source.

In a preferred embodiment, at least one of the angular arrangements is arranged in a parallel orientation to the plane of emission of the radiation source such that the axis extending vertically from the plane of the emission of the radiation source extends between the at least two angular arrangements and at least one of the angular arrangements is arranged at an angle of 90° at right angles to the axis extending vertically from the plane of the emission of the radiation source.

In a special embodiment, all of the at least two angular arrangements are arranged at an angle to the axis extending vertically from the plane of the emission of the radiation source such that the axis extending vertically from the plane of the emission of the radiation source extends between the at least two angular arrangements and each of the at least two angular arrangements is sloped at an angle towards the axis extending vertically from the plane of the emission of the radiation source. The slopes of the angles of each of the at least two angular arrangements to the axis extending vertically from the plane of the emission of the radiation source between the at least two angular arrangements may be different from one another or nearly identical. Thus, configurations of 60° are possible for one of the at least two angular arrangements and configurations of 30° are possible for other of the at least two angular arrangements, as are configurations of 45° for both of the at least two angular arrangements to the axis extending vertically from the plane of the emission of the radiation source between the at least two angular arrangements.

This configuration of the at least two angular arrangements leads to a slope of the at least two angular arrangements in relation to one another. This slope offers the advantage that a range of overlap is present between the beam paths of the radiation source to the detector elements between the at least two detector elements.

This range of overlap is obtained vertically from the plane in which the detector elements are arranged in the direction of the radiation source. Due to the angles, gas molecules, water vapor, condensate or even other impurities, for example, dust, are present in the beam paths of both detector elements, so that the influence of water vapor, condensate or even other impurities is reflected in the measured signal, for example, as an amplitude attenuation of the measured values in both the measuring channel and the reference channel. This leads to the possibility of eliminating the influence of moisture (water vapor, condensate) or even other impurities by forming the ratio of the signals of the reference channel and of the measuring channel. The range of overlap can be defined by selecting respective angles of the angular arrangements of the measuring channel detector element/bandpass filter element and reference channel detector element/bandpass filter element in relation to one another as well as in relation to the axis extending between the at least two angular arrangements.

In conjunction with the selection of a vertical distance between the radiation source and the angular arrangements, the configuration of the range of overlap can be further varied and defined with extension in space, flat overlap, effective overlap volume for the measured gas.

For example, the absorption properties of the measured gas to be measured can be taken into account and the desired concentration measurement ranges of the measured gas can be influenced by the above-described configurations of the angular arrangements and of the vertical distance in the device for determining the concentration of at least one gas component in a breathing gas mixture.

In a preferred embodiment, each of the at least two detector elements is arranged at a first distance $l_1$ to the axis extending preferably centrally between the at least two angular arrangements in a range of 0.1 mm to 10 mm.

In a preferred embodiment, each of the at least two bandpass filter elements arranged at the at least two detector elements is arranged at a second distance $l_2$ to the vertical axis extending preferably centrally between the at least two angular arrangements in a range 0.1 mm to 10 mm.

In a preferred embodiment, the at least two angular arrangements are arranged at spaced locations from one another in a range of 0.1 mm to 10 mm.

In another preferred embodiment, the detector array with the at least two detector elements and the at least two bandpass filter elements arranged at the at least two detector elements are arranged at a third distance (detector array to source distance) $l_3$ in a range of 0.1 mm to 10.0 mm, the third distance $l_3$ being obtained as a distance directly in the range of or along the axis extending between the at least two angular arrangements.

In a preferred embodiment, the detector array with the at least two detector elements and with the at least two bandpass filter elements arranged at the at least two detector elements are arranged on the same side adjacent to the radiation source, and the radiation source is arranged centrally on the axis extending between the at least two angular arrangements between the at least two detector elements with the at least two bandpass filter elements arranged at the at least two detector elements.

At least one optically reflecting reflector element preferably having a flat configuration is arranged here opposite the radiation source and opposite the at least two detector elements with the at least two bandpass filter elements arranged at the at least two detector elements at a third distance $l_{3'}$ in a range of 0.1 mm to 5.0 mm, wherein the third distance $l_{3'}$ is obtained as a distance directly in the range of or along the axis extending between the at least two angular arrangements.

The bandpass filter elements are configured for the optical filtering of infrared light in a transmission range of the wavelength range of 2.5 µm to 14 µm.

Transmission ranges for gases as listed in Table 1 below are thus made possible with such bandpass filter elements.

TABLE 1

| No. | Gas species | Wavelength range | |
|---|---|---|---|
| 1 | Carbon dioxide | 4.2 µm to 4.4 µm | $CO_2$ |
| | Laughing gas | 7.8 µm to 9.0 µm | $N_2O$ |
| | Methane | 3.1 µm to 3.5 µm | $CH_4$ |
| | Ethane | 3.2 µm to 3.6 µm | $C_2H_5$ |
| | Halothane | 8 µm to 10 µm | $C_2HBrClF_3$ |
| | Isoflurane | 8 µm to 10 µm | $C_3H_2OClF_5$ |
| | Enflurane | 8 µm to 10 µm | $C_3H_2ClF_5O$ |
| | Sevoflurane | 8 µm to 10 µm | $C_4H_3F_7O$ |
| | Desflurane | 8 µm to 10 µm | $C_3H_2F_6O$ |
| | Acetone | 8 µm to 10 µm | $C_3H_6O$ |
| | Ethyl alcohol | 8 µm to 10 µm | $C_2H_5OH$ |

The gases laughing gas, halothane, sevoflurane and desflurane are used during the performance of anesthesia, for example, during surgical procedures to anesthetize patients. Acetone is formed as a possible metabolite in patients and is thus contained, for example, in the air exhaled by diabetics. Ethyl alcohol may be present, for example, in the air exhaled by patients who are under the influence of alcohol.

In another preferred embodiment, the radiation source is configured as a flat radiator or as a diaphragm radiator or as a light-emitting diode (LED) with an essentially planarly configured radiating surface. Such a flat or diaphragm radiator with a planar radiation element or light-emitting diode (LED) is configured with an essentially planarly configured radiating surface for uniform radiation over the radiating surface.

The radiating surface of the flat radiator or of the diaphragm radiator as well as the radiating surface of an essentially planarly configured light exit surface of the light-emitting diode are preferably configured in a range of 2.0 mm² to 10 mm².

In another preferred embodiment, the detector elements are configured as thermopiles or thermocouples.

In another preferred embodiment, the detector elements are configured as semiconductor detectors, for example, InAsSb detectors (indium-arsenic-antimony detectors).

In another preferred embodiment, the detector elements are configured as pyrodetectors.

In another preferred embodiment, the detector elements are configured as bolometers.

The facts that thermocouples, thermopiles, pyrodetectors and bolometers can be manufactured in a cost-effective manner and can be used as thermal detectors in a broad wavelength range of 3 µm to 10 µm can be mentioned as advantages of these elements.

The fact that the measuring sensitivity can be adapted very well to the desired wavelength range can be mentioned as an advantage of semiconductor detectors.

In another preferred embodiment, a plurality of more than two detector elements with respective bandpass filter elements arranged thereon are arranged to form a circular or rectangular array, for example, of lateral surfaces of a truncated pyramid, together around a center.

The truncated pyramid is shaped such that it has, quasi as a funnel, a shape of an inverted truncated pyramid or a shape of a cloverleaf or of the calyx of a tulip. In a special variant of this additional preferred embodiment, the detector array has four angular arrangements with detector elements and bandpass filter elements in a spatial arrangement in the form of four lateral surfaces of a rectangular or square truncated pyramid. Measurements with a plurality of measured gases can be detected in this manner, for example, by means of three measuring channels in relation to a reference channel.

It is thus possible, for example, to carry out measurements of carbon dioxide ($CO_2$), laughing gas ($N_2O$) and a volatile anesthetic, for example, halothane ($C_2HBrClF_3$), isoflurane ($C_3H_2OClF_5$) in relation to the reference channel advantageously in a single device for determining the concentration of at least one gas component in breathing gas mixture.

In another preferred embodiment, the detector array and the radiation source form a flow guide element suitable for guiding inhaled gas and/or exhaled gas for flow guiding in a flow channel in the device for determining the concentration of at least one gas component in a breathing gas mixture. The inhaled gas and/or exhaled gas are sent through the flow guide element and they pass in the process through the beam pass between the radiation source and the at least two angular arrangements with the at least two detector elements and with the bandpass filter elements arranged thereon. The gas concentration is detected now in the main stream.

A configuration of such an embodiment is, for example, a device for measuring carbon dioxide in the exhaled gas of a patient as a device located directly at the area of the patient's mouth, which is often also called a so-called "mainstream $CO_2$ sensor."

Another configuration of such an embodiment is, for example, an analysis unit for measuring carbon dioxide and other exhaled gases, especially anesthetic gases. The measurement is carried out in the exhaled gas of a patient by means of a device in which a quantity of gas is drawn off or delivered continuously directly in the area of the mouth via a tube of a small diameter to the analysis unit by a pump arranged in the analysis unit and the quantity of gas is analyzed there with respect to the gas composition and the gas concentration. Such a measuring method is also often called a so-called "suctioning gas measurement" or a so-called "sidestream anesthetic gas monitoring."

In another preferred embodiment, the device for determining the concentration of at least one gas component in a breathing gas mixture has a flow guide element for guiding the flow in a flow channel, in or at which the detector array, the radiation source and the optically reflecting element are arranged. The flow guide element has a component protruding into the flow channel. A part of the inhaled gas and/or exhaled gas is guided through this component in the flow guide element as a side stream and it now passes through the beam path between the optically reflecting element and the at least two angular arrangements with the at least two detector elements and with the bandpass filter elements arranged thereon. The gas concentration is detected here in the part of the main stream in a side stream.

Such a component, for example, in the form of a so-called T-piece, can guide the part of the main stream centrally in the flow guide element such that measured gas, which is representative of quantities of gas in the center of the flow guide element, is used for the concentration measurement.

Such a component, for example, in the form of an insert or plug-in unit arranged laterally on the flow guide element at the edge of the flow guide element, can guide the part of the main stream such that measured gas that is representative of quantities of gas in a lateral edge of the flow guide element is used for the concentration measurement.

The overall size of the device for determining the concentration of at least one gas component in a breathing gas mixture plays a rather important role for the application of gas measurements in the field of anesthesia, especially for the "sidestream" application. In conjunction with the overall sizes of the radiation source with a radiating surface in the preferred range of 2.0 $mm^2$ to 10.0 $mm^2$ of the detector elements (bolometer, microbolometer, microbolometer arrays, pyrodetectors, thermocouples, thermopiles, semiconductor detectors) and bandpass filter elements with surfaces in a preferred range of 0.5 $mm^2$ to 20 $mm^2$ and with the arrangement of the at least two detector elements in relation to one another at distances in a preferred range smaller than 10 mm, the distance $l_3$ in a preferred range of 0.1 mm to 10 mm between the radiation source and the detector elements and bandpass filter elements as well as the distance $l_{3'}$ in the range of 0.1 mm to 5.0 mm between the radiation source and the optically reflecting element (mirror, reflector) make it possible to obtain an overall size for the device for determining the concentration of at least one gas component in a breathing gas mixture with a small measurement volume in a range of less than 0.4 mL, for example, 0.05 mL to 0.2 mL.

In case of "suctioning gas measurement" with a suction volume flow of 50 mL/min to 200 mL/min with the pump arranged in the device, the duration for the exchange of the measured volume in the device for determining the concentration of at least one gas component in a breathing gas mixture will be 0.1 sec to 0.5 sec.

Compared to respiration rates of humans in the range of about 6 breaths per minute to 24 breaths per minute (corresponding to 0.1 to 0.4 breaths per second), the device for determining the concentration of at least one gas component in a breathing gas mixture, which is proposed by this invention, makes possible a measuring time resolution that makes it possible, in conjunction with a fittingly selected scanning rate, to detect concentration changes in the breathing gas as measured data resolved for individual breaths.

Generally, but also for a so-called "mainstream measurement," for example, in the form of the above-described T-piece as a component for guiding a side stream, the overall size also plays another important role, because, due to the distances, not only is a small measurement volume made possible, but the optical path lengths between the detector elements and the radiation source can be kept short as well. As a result, measured data that have a sufficient signal level with a good signal-to-noise ratio (SNR) can be detected at the detector elements, so that a high measuring sensitivity with robust signal quality is available, which make possible a largely noise-free, high measuring resolution, e.g., with a 16-bit quantification or finer (20 bits, 24 bits).

Due to the overlap of the measuring channel and the reference channel, it is advantageously achieved that the measured data, which are resolved for individual breaths and are detected for effects that affect both the measuring channel and the reference channel in a similar manner, for example, changes in the temperature of the measured gas, impurities, water vapor, moisture, contaminations of the radiation source or of the reflector element, are available directly and without undue delay at the time of the actual physical measurement without major effort for further signal processing and correction of measured data, for example, moisture and/or temperature compensation, on the basis of externally provided moisture and/or temperature data.

The embodiments described represent, both in themselves and in combination or combinations with one another, special embodiments of the device for determining the concentration of gas components in a breathing gas mixture. All embodiments and possible additional embodiments arising through combination or combinations of a plurality of embodiments and their advantages are also equally covered by the inventive idea, even though not all possibilities of combinations of embodiments are described specifically in detail for this.

The present invention will be explained in more detail below by means of the following figures and the corresponding descriptions of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
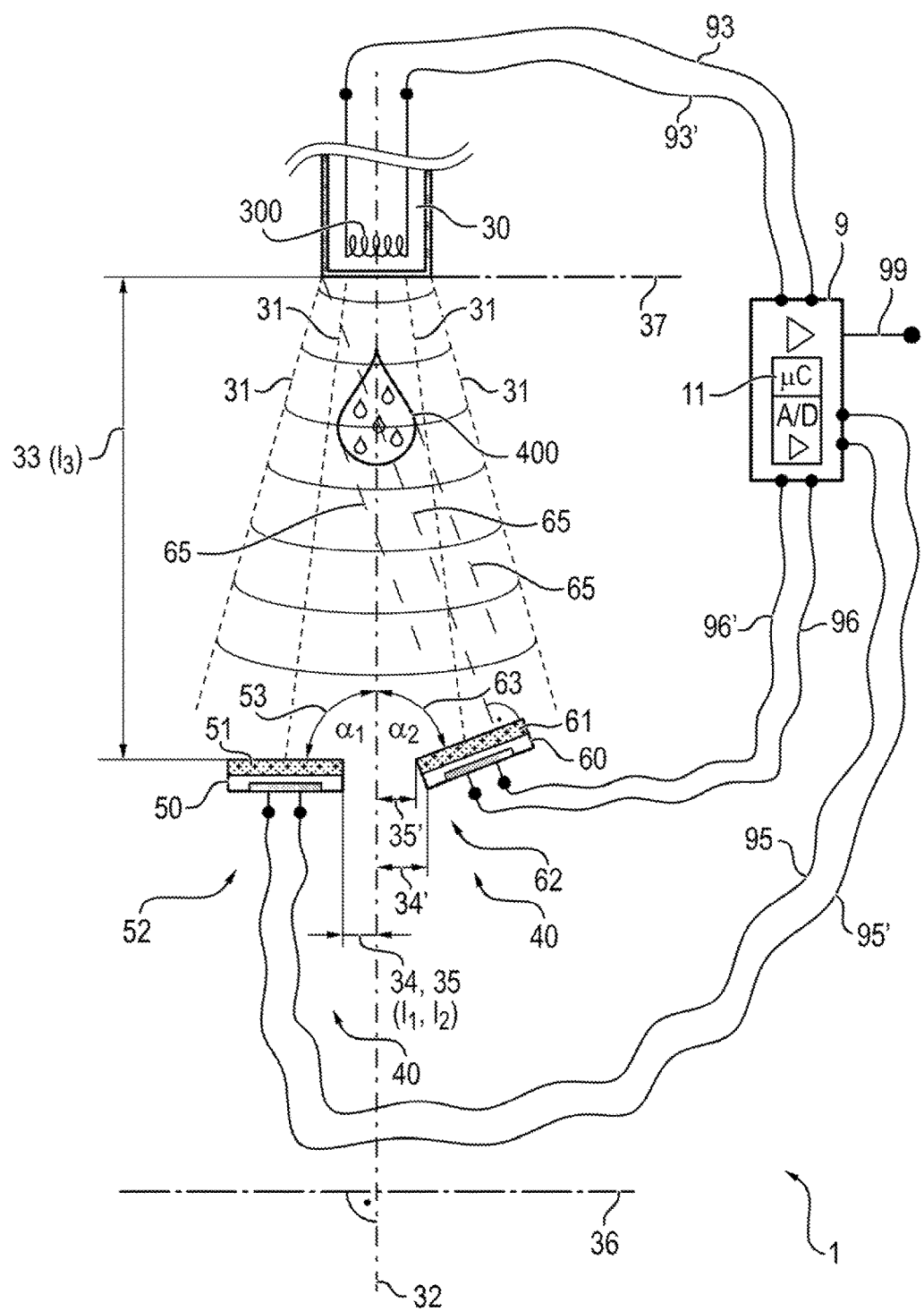
FIG. 1a is a first schematic view of a device for concentration determination.

Referring to the drawings, FIG. 1a shows a first schematic view of a device 1 for determining the concentration of at least one gas component in a breathing gas mixture. The device 1 shown has a radiation source 30 with a radiation element 300. A detector element 50 and a detector element 60 are arranged opposite the radiation source 30 at a vertical distance $l_3$ 33. Bandpass filter elements 51, 61 are arranged at the detector elements 50, 60. The bandpass filter elements 51, 61 are preferably configured as bypass filter elements that are transparent to a predefined wavelength range of the radiation 31 emitted by the radiation source 30. This FIG. 1a shows a coordinate system with vertical reference axis 32 and with a horizontal reference axis 36, to which system reference is made in the description of the positions of the components in relation to one another. Thus, a radiation takes place from the radiation source 30 out of a horizontal plane of radiation 37, the horizontal plane 37 being parallel to the horizontal reference plane 36.

A control unit 9 is provided, which is connected to the radiation element 300 by means of control lines 93, 93'. Furthermore, the control unit 9 is connected to the detector element 60 by means of control lines 96, 96'. The control unit 9 is furthermore connected to the detector element 50 by means of control lines 95, 95'. The detector element 50 together with the corresponding filter element 51 forms an angular arrangement 52. The detector element 60 together with the corresponding filter element 61 forms an angular arrangement 62. The angular arrangements 52 and 62 together form a detector array 40, which functionally forms the device 1 for determining the concentration of a gas component in conjunction with the radiation source 30 and the control unit 9. The arrangement of the detector array 40 in relation to the vertical axis 32 and to the horizontal reference axis 36 is determined by distances and angles of the angular arrangements 52, 62.

The angular arrangement 52 is configured in this FIG. 1a in a parallel arrangement in relation to the horizontal reference axis 36 as well as to the horizontal plane of the radiation 37. An angle $\alpha_1$ 53 of the angular arrangement 52 to the vertical reference axis 32 equaling 90° is thus obtained. A horizontal distance $l_1$ 34 of the detector elements 50 to the central axis 32 is obtained in the detector array 40. A distance $l_1$ 34' to the central axis 32 is obtained in the detector array 40 for the detector element 60. A distance $l_2$ 35 of the bandpass filter element 51 to the central axis 32 is obtained in the detector array 40. Furthermore, a distance $l_2$ 35' is obtained for the filter element 61 to the central axis 32 in the detector array 40. Due to the arrangement of the angular arrangement 52 at an angle of 90° to the central axis 32, the distances $l_1$ 34 and $l_2$ 35 to the central axis are identical for the detector element 50 and the filter element 51.

The angular arrangement 62 is configured sloped to the central axis 32 at an angle of $\alpha_2$ 63. The angle $\alpha_2$ 63 is defined here in an angle range markedly lower than 90° to the central axis 32. Due to the slope of the angular arrangement 62 with the detector element 60 and with the filter element 61 at an angle $\alpha_2$ 63, a range of overlap 65 is obtained in the radiation 31 for the radiation 31 emitted by the radiation source 30 along the vertical distance $l_3$ 33 between the radiation source 30 and the detector array 40. This range of overlap 65 is obtained vertically from the plane of the angular arrangement 62 in the direction of the radiation source 30. Due to the angles $\alpha_1$ 53 and $\alpha_2$ 63, the situation arises, for example, for gas molecules or condensate (moisture, such as water vapor or water droplets) 400, which are shown in this FIG. 1a as an example on the central axis 32 in the vicinity of the radiation source 30, that the radiation 31 of the radiation source passes through this gas molecule 400 and it becomes effective as radiation 31 to both the detector element 50 and the detector element 60. It is thus ensured that, for example, moisture (condensate) 400 attenuates the radiation to the detector element 50 as well as to the detector element 60 in the same manner. This leads to the possibility of eliminating the effect of moisture from the formation of the ratio of the signals of the detector element 50 and of the detector element 60. The range of the overlap can be defined by selecting the angles $\alpha_1$ 53 and $\alpha_2$ 63 in relation to one another as well as to the vertical central axis 32. The extension of the range of overlap 65 is still defined in conjunction with the selection of the vertical distance $l_3$ 33 between the radiation source 30 and the detector array 40.

The control unit 9 analyzes the signals of the detector elements 50, 60 by means of suitable electronic components 11 (amplifiers, analog-to-digital converters, microcontroller) and provides an output signal. The output signal 99 is representative here of the signals detected by the detector elements 50, 60 as well as of the ratio of the detected signals and hence it is also representative of a gas concentration derived from these signals or from the signal ratio.

Figure 1B:
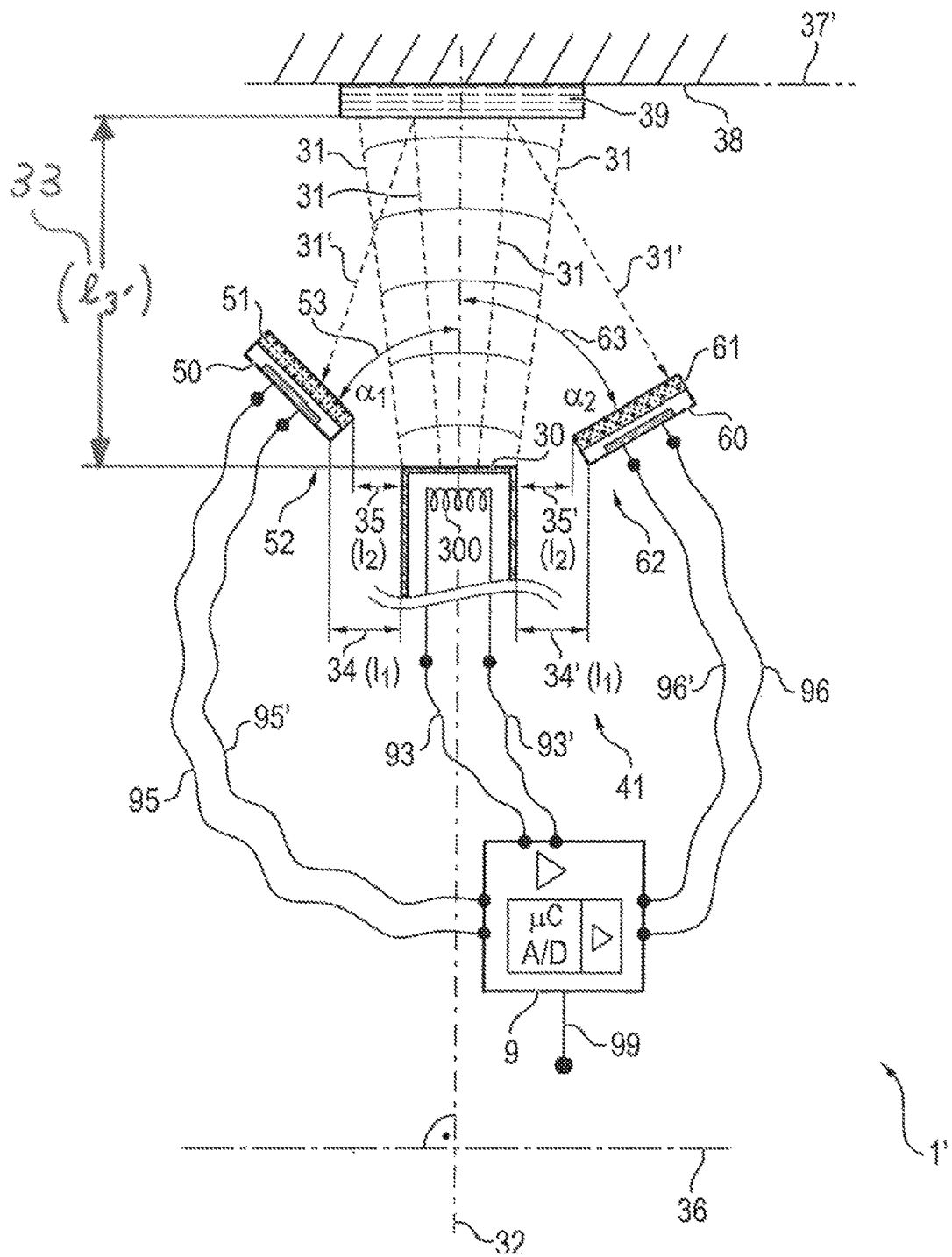
FIG. 1b is another, second schematic view of a device for concentration determination.

FIG. 1b shows another, second schematic view of a device 1' for determining the concentration of at least one gas component in a breathing gas mixture. Components that are identical in FIG. 1a and FIG. 1b are designated by the same reference numbers in this FIG. 1b as the correspondingly equivalent elements in FIG. 1a.

With the other, second schematic view, FIG. 1b shows a modified variant of FIG. 1a. Unlike in FIG. 1a, the radiation source 30 is arranged in FIG. 1b on the same side as the optical elements and the detectors. The device 1' shown has a radiation source 30 with a radiation element 300. A detector element 50 and another detector element 60 are arranged directly adjacent to the radiation source 30. Bandpass filter elements 51, 61 are arranged at the detector elements 50, 60. A reflector 39, for example, a plane mirror, is arranged as a reflecting optical device opposite the radiation source 30. The reflector 39 acts as a mirror for the radiation 31 emitted by the radiation source 30 and brings about a reflection of a reflected radiation 31' towards the bandpass filter elements 51, 61 as well as to the detector elements 50, 60. The bandpass filter elements 51, 61 transmit light in a predefined wavelength range. A coordinate system with vertical reference axes 32 and horizontal reference axes 36 is shown in this FIG. 1b. These axes are used, in a similar manner as in the description of FIG. 1a, as a reference for the position of the components in relation to one another and in space. A control unit 9 is provided, which is connected to the radiation element 300 of the radiation source 30. The arrangement by means of control line 93, 93' and 96, 96' as well as 95, 95' for connecting the control unit 9 to the detector elements 60, 50 corresponds to the arrangement according to FIG. 1a and to the corresponding description, to which reference shall be made here. The detector element 50 forms, together with the corresponding filter element 51, an angular arrangement 52. The detector element 60 likewise forms an angular arrangement 62 with the corresponding filter element 61. These angular arrangements 52, 62 form, together with the radiation source 30, a detector array 41, which functionally forms the device 1' for determining the concentration of a gas component in conjunction with the control unit 9 and the reflector 39. The arrangement of the detector array 41 in relation to the axes 32, 36 is defined by distances and angles of the angular arrangement 52, 62. A horizontal distance $l_1$ 34 of the detector element 50 from the central axis 32 is obtained in the detector array 41. A distance $l_1$ 34' from the central axis 32 is obtained in the detector array 41 for the detector element 32. A distance $l_2$ 35 of the bandpass filter element 51 from the central axis 32 is obtained in the detector array 41. Furthermore, a distance $l_2$ 35' from the central axis 32 is obtained in the detector array 41.

The angular arrangements 52, 62 are always sloped to the central axis 32 at angles $\alpha_1$ 53 and $\alpha_2$ 63 in this FIG. 1b.

Figure 2:
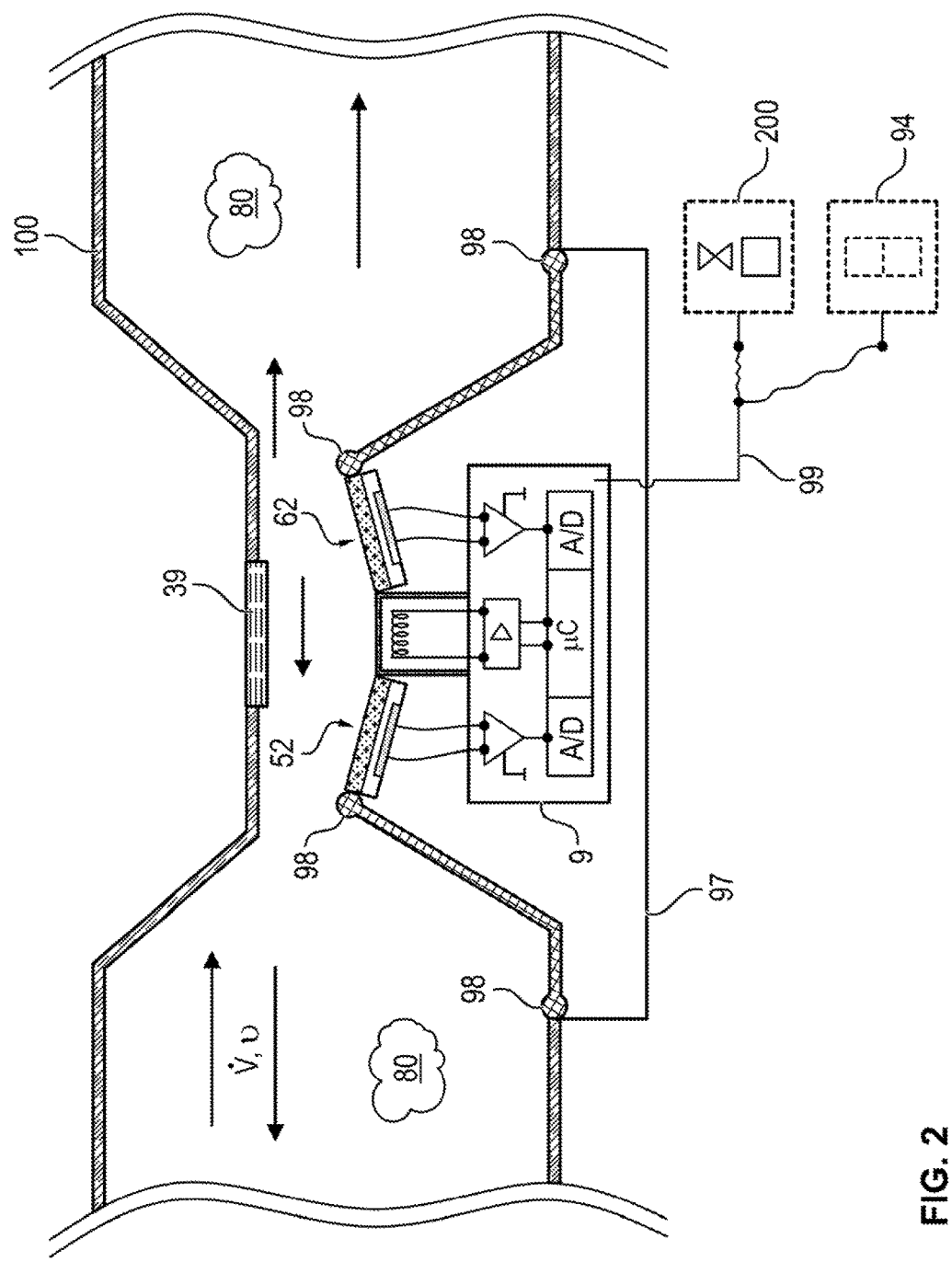
FIG. 2 is an arrangement of a device for concentration determination at a flow guide element.

The angles $\alpha_1$ 53 and $\alpha_2$ 63 have an angle range markedly smaller than 90° relative to the central axis 32. The angles $\alpha_2$ 63 and $\alpha_1$ 53 have, for example, different angular dimensions in this FIG. 1b, but the idea of the present invention also covers the case in which $\alpha_2$ 63 and $\alpha_1$ 53 can also have identical angular dimensions to the central axis 32. Due to the slope of the angular arrangement 52 with the detector element 50 and with the filter element 51 at the angle $\alpha_1$ 53 and due to the slope of the angular management 62 with the detector element 60 and with the filter element 61 at the angle $\alpha_2$ 63, ranges of overlap in a reflected radiation 31' are obtained for the radiation 31 emitted by the radiation source 30 along the vertical distance between the radiation source 30 and the detector array 41 after reflection by means of the reflector 39. The angular arrangements 52, 62 are configured in reference to the horizontal reference axis 36, the central axis 32 and a horizontal plane of the light reflection 37', which is arranged parallel to the horizontal reference axis 36. The range of overlap, which is obtained on the basis of the angular arrangements 52 and 62, causes impurities or condensate, which are present, for example, in the vicinity of the reflector 39 in the reflected radiation 31, to influence, i.e., possibly attenuate, the detector element 50 in the same manner as the detector element 60. This leads to the possibility, as described in connection with FIG. 1a, of eliminating the influence of moisture 400 (FIG. 1a) or impurities from the ratio of the signals of the detector element 50 and of the element 60. The range of overlap can be defined by selecting the angles $\alpha_1$ 53 and $\alpha_2$ 63 in relation to one another as well as to the vertical central axis 32. Unlike in FIG. 1a, a longer, in the simplest case twice as long a beam path is obtained in this FIG. 1b for the path of the radiation 31 towards the reflector 39 and to the reflected path of the reflected radiation 31' to the detector elements 50, 60. The consequence of this is that the light beams reaching the detector elements 50, 60 are of a lower intensity than in FIG. 1a. This causes a difference concerning the sensitivity of the device 1' for determining the concentration of a gas component in this FIG. 1b. The analysis of the signals of the detector elements 50, 60 in the control unit 9 is carried out in the same manner as described in connection with FIG. 1a, by means of suitable electronic components 11. The control unit provides an output signal 99, which is representative of the signals of the detector elements 50, 60 or of the ratio of the signals of the detector elements 50, 60. The output signal 99 thus provides a gas concentration derived from the signals on the basis of the detected signals of the detector elements 50, 60 for further processing, for example, for a display unit 94 (FIG. 2).

Figure 1C:
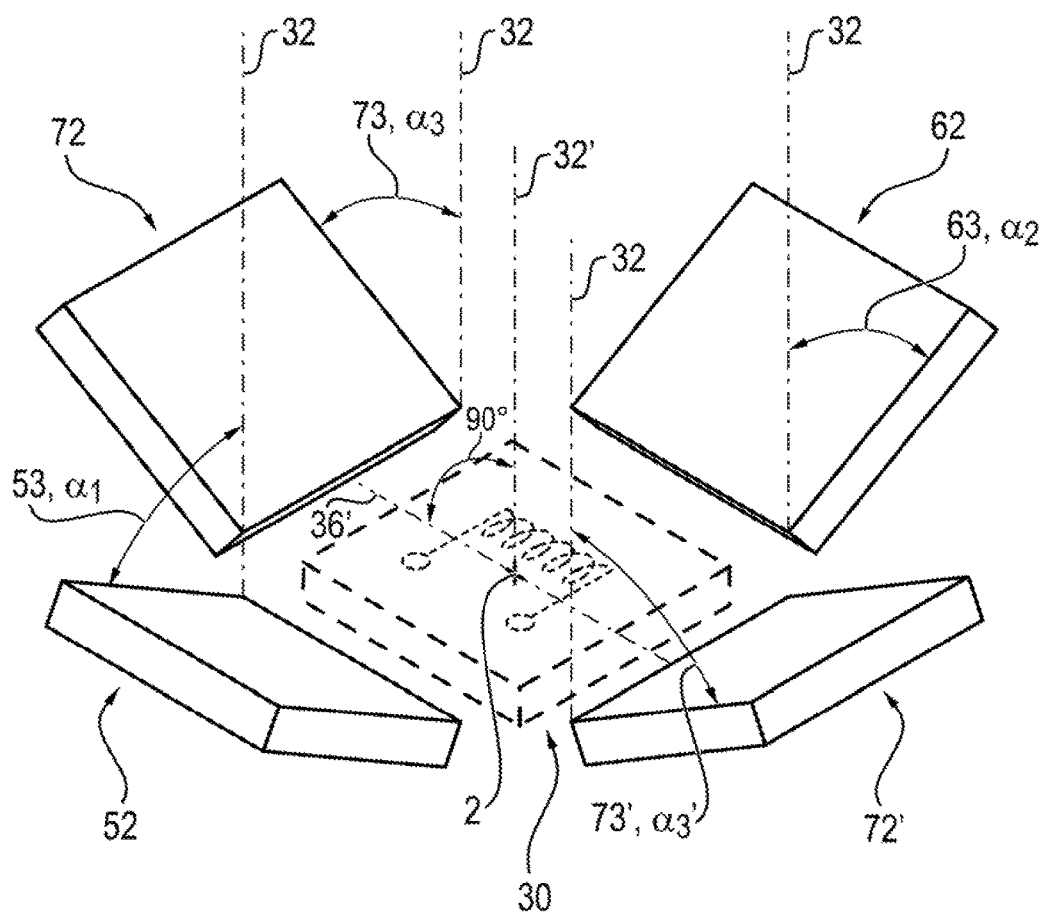
FIG. 1c is a schematic view of a variant of a device for concentration determination according to FIG. 1a or 1b.
Figure 1C:
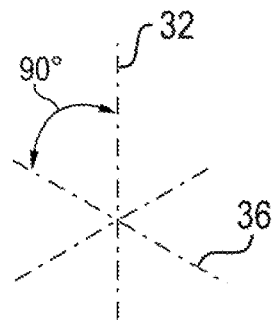

FIG. 1c shows a schematic view of a variant of a device for determining the concentration according to FIG. 1a or 1b. Identical components in FIGS. 1a, 1b and FIG. 1c are designated in this FIG. 1c by the same reference numbers as the correspondingly equivalent components in FIGS. 1a and 1b.

FIG. 1c shows a variant according to FIG. 1a or FIG. 1b. FIGS. 1a and 1b show two basic variants of the configuration of detector elements 50, 60, radiation source 30 in conjunction with or without a reflector 37. FIG. 1c shall show a variant in which not only two detector elements 50, 60 are arranged as a device for gas measurement, but a total of more than two detector elements are arranged in a circular or rectangular configuration in relation to one another. Such a configuration with a plurality of detector elements makes it possible to make a measurement with a plurality of measured signals, for example, of three or more gases, with three or more detector elements associated with the measured gases in relation to a reference by means of a reference detector element. A funnel, which has the shape of an inverted truncated pyramid with a rectangular or square base or frustum surface, is shown as the geometric configuration in this FIG. 1c.

FIG. 1c is configured for this as follows:

A total of four angular arrangements 52, 62, 72, 72' are configured structurally around a center 2 in an arrangement sloped towards a central axis 32 at angles $\alpha_1$ 52, $\alpha_2$ 62, $\alpha_3$ 73, $\alpha_3$, 73'. The horizontal axes 36 as well as 36' and the vertical axes 32 are always shown in FIG. 1c arranged at the angular arrangements 52, 62, 72, 72' in order to make it possible to clearly show the spatial arrangement in this FIG. 1c. The axes 32, 32', 36, 36' illustrate here the same spatial coordinate system as is shown in FIGS. 1a and 1b.

In a configuration of FIG. 1c according to FIG. 1b with the device 1' for determining the concentration of a gas component, a radiation source 30, indicated by broken lines, is arranged centrally between the angular arrangements 52, 62, 72, 72'. Not shown in this FIG. 1c, a reflector element is again necessary opposite this radiation source 30. Such a configuration is obtained, as can be seen in FIG. 1b, with an arrangement of a reflector 39 (FIG. 1b) at a wall located opposite the radiation source 30 with a horizontal plane of the light reflection 37' (FIG. 1b). The radiation source 30 is shown here directly at the center 2 with a radiation element 300, indicated here by a coil drawn by broken lines.

The radiation source 30 at the center 2 is omitted in a configuration of FIG. 1c with a device 1 for determining the concentration of a gas component according to FIG. 1a. The radiation source would be arranged in such a configuration opposite the angular arrangements 52, 62, 72, 72', and the area around the center 2 would be free of measuring or optical components (52, 62, 72, 72'). As an alternative to this, a configuration may be selected, in which this area around the center 2 does not remain free. A configuration can then be selected as a variation in which another angular arrangement is made possible there. This additional angular arrangement is not shown specifically in this FIG. 1c, but it comprises all the features with a detector element and with a filter element and is arranged planarly to the horizontal plane 36 or 36' as a reference detector element. Such an additional angular arrangement may be used, for example, to provide a reference signal. The variant is now obtained in which four rather than the three different gases can be detected with the angular arrangements 52, 62, 72, 72' in reference to the one reference detector element, which is arranged centrally between the other four detector elements. A compensation of interferences due to the common range of overlap 65 (FIG. 1a) of the reference detector element with all four angular arrangements 52, 62, 72, 72', which is not shown in this FIG. 1c for the sake of clarity, is thus achieved by means of the reference detector element.

This advantageously leads to an embodiment in which interferences, impurities, condensate and other impurities present in the radiation are equally reflected in all three measured signals and in the reference signal, so that an optimal compensation of these effects is ensured.

Figure 3:
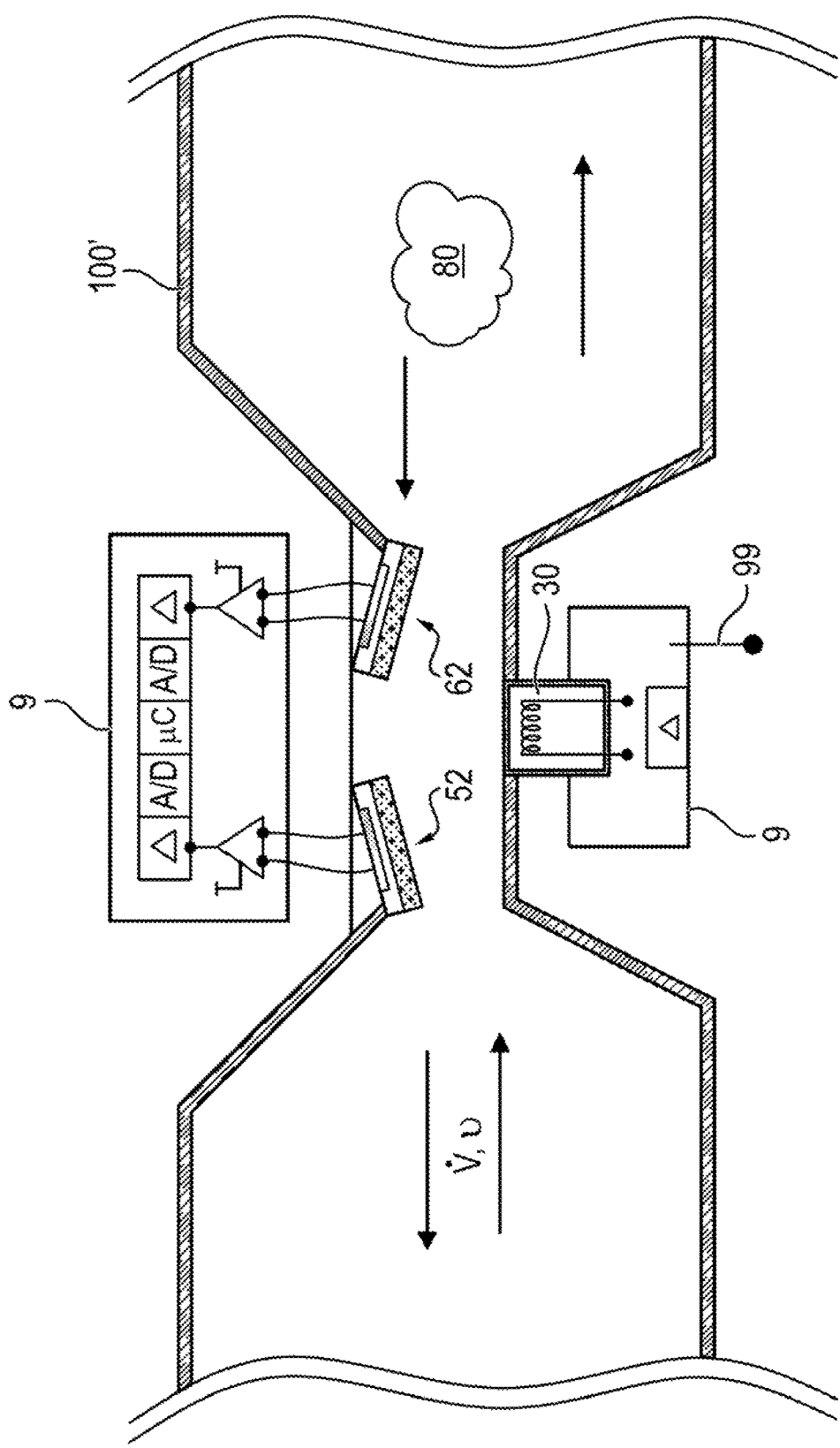
FIG. 3 is another arrangement of a device for concentration determination at a flow guide element.
Figure 4:
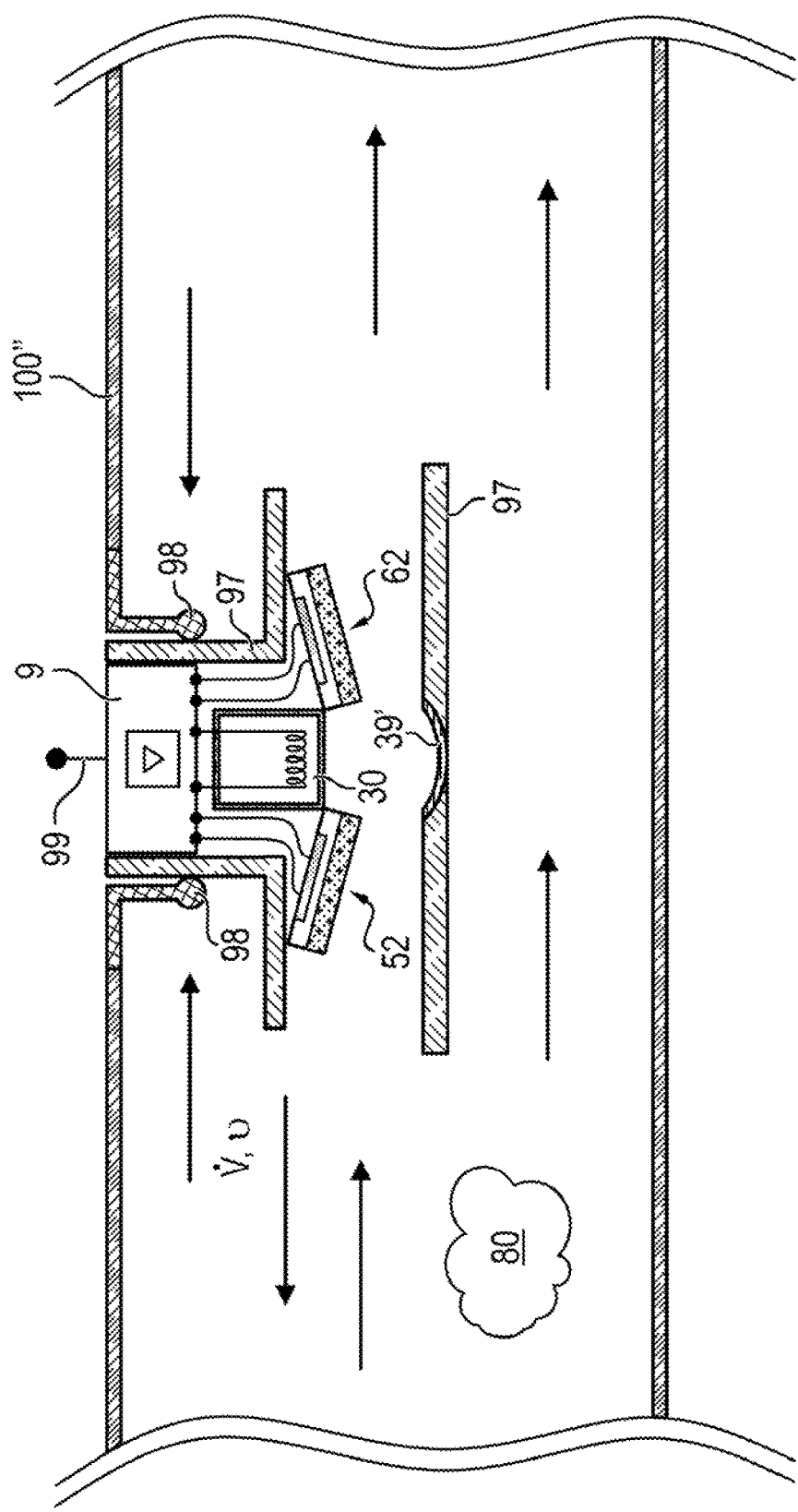
FIG. 4 is a flow guide element a device for concentration determination.

FIGS. 2, 3, 4 show arrangements of a device for determining the concentration according to FIGS. 1a, 1b, 1c at a flow guide element. FIGS. 2, 3, 4 shall be described in a joint description of the figures concerning the features shared in common with one another, but also in respect to the differences from one another.

Identical components in FIGS. 2, 3, 4 and in FIGS. 1a, 1b, 1c are designated by the same reference numbers as the correspondingly equivalent components in FIGS. 2, 3, 4 as well as in FIGS. 1a, 1b, 1c.

FIG. 2 shows a device 1' for determining the concentration of a gas component (FIG. 1b) in a flow guide element 100. The flow guide element 100 is configured to feed a flow with a quantity of gas 80 for a measurement by means of the device 1' (FIG. 1b). Angular arrangements 52, 62 are shown in conjunction with a radiation source, with a radiation element and with a control unit 9. The angular arrangements 52, 62 with the radiation source and with the control unit 9 are arranged in a holding element 97, which is coupled with the flow guide element 100 by means of sealing elements 98. The mode of operation of the arrangement according to FIG. 2 is as described in connection with FIG. 1*b*.

FIG. 4 shows an arrangement comparable to that in FIG. 2 in a flow channel 100' with a device 1' for determining the concentration of a gas component. A holding element 97, which is inserted into the flow guide element 100" by means of sealing elements, is present here as well. Unlike in FIG. 2, only a partial quantity in the form of a side stream of the quantity of gas flowing in the flow guide element 100" enters the device 1' (FIG. 1*b*) for determining the concentration of a gas component in the flow guide element 100" in this FIG. 4. This FIG. 4 thus shows a measurement in a so-called bypass. Just as in FIG. 2, a reflector 39', this time shown in an arched configuration, is arranged opposite the radiation source 30 in this FIG. 4 as a part of the holding element 97.

The device 1' (FIG. 1*b*) for determining the concentration of a gas component in a side stream is arranged in this FIG. 4 in the bypass with the arrangement of the holding element 97 as an insert in the flow guide element 100", configured in the form of a "T-piece," is arranged and acts for the purpose of measurement nearly in the flow center of the flow guide element 100", i.e., essentially in the center of the flow guide element 100". As an alternative and in addition, an arrangement of the holding element 97, in which the device 1' (FIG. 1*b*) for determining the concentration of a gas component is not arranged and acts for the purpose of measurement in the center of the flow, but in the marginal area of the flow guide element 100", is shown this FIG. 4. A configuration of the bypass in the area of an edge flow in the marginal area of the flow guide element 100" is thus obtained.

Unlike FIG. 2 as well as FIG. 4, FIG. 3 shows a device 1 for determining the concentration of a gas component according to FIG. 1*a* in a flow channel 100'. The radiation source 30 is arranged opposite two angular arrangements 52, 62 at a flow guide element 100'. The angular arrangements 52, 62 and of the radiation source 30 are arranged opposite at a point of the flow guide element 100 at which the flow cross section is reduced in the form of a Venturi tube. It is necessary in this configuration according to FIG. 3 to provide elements of a control unit 9 from two sides. This makes it possible both to operate the angular arrangements 52, 62 with the detector elements 50, 60 (FIG. 1*a*) and to amplify the signals. In addition, the control unit 9 is used to actuate the radiation source 30 and to send an output signal 99.

An output signal 99, which is, as was explained above in FIGS. 1*a* and 1*b*, representative of a detected gas concentration, is provided in FIGS. 2, 3, 4.

Unlike FIG. 4, FIG. 3 as well as FIG. 2 are configured such that the measurement of the gas concentration of the quantity of gas 80 is not carried out in a bypass stream, but directly in the main stream. FIG. 2 shows a medical device 200 as well as a display unit 94 by broken lines as respective optional components. These optional components represent exemplary possibilities of sending the output signal 99 for further processing and use.

These optional components 200, 94 are not shown in FIGS. 3 and 4, but they shall likewise be considered to be included in the configurations according to these FIGS. 3 and 4.

While specific embodiments of the invention have been shown and described in detail to illustrate the application of the principles of the invention, it will be understood that the invention may be embodied otherwise without departing from such principles.

APPENDIX

List of Reference Designations

1, 1' Device for determining the concentration of a gas component
2 Center (intersection of the axes 32' and 36')
9 Control unit
11 Electronic components
30 Radiation source
31 Radiation
31' Reflected radiation
32, 32' Vertical (length) axis, central axis, vertical reference axis
33 $l_3$, $l_{3'}$ vertical distance
34 $l_1$ distance of the detector element 50 from the central axis 32
34' $l_1$ distance of the detector element 60 from the central axis 32
35 $l_2$ distance of the filter element 51 from the central axis 32
35' $l_2$ distance of the filter element 61 from the central axis 32
36, 36' Horizontal reference axis
37 Horizontal (width) plane of radiation
37' Horizontal (width) plane of light reflection
38 Wall
39, 39' Reflector, mirror element
40 Detector array
41 Detector array, reflective
50 Detector element
51 Bandpass filter element
52 Angular arrangement
53 Angle $\alpha_1$
60 Detector element
61 Bandpass filter element
62 Angular arrangement
63 Angle $\alpha_2$
65 Range of overlap
72 Angular arrangement
72' Angular arrangement
73 Angle $\alpha_3$
73' Angle $\alpha_{3'}$
80 Quantity of gas, gas concentration
93, 93' Control line to the radiation element 300
94 Display unit
95, 95' Data line, signal line
96, 96' Data line, signal line
97 Holding element
98 Insert, sealing element
99 Output signal
100, 100', 100" Flow guide element
200 Medical device, ventilator, anesthesia device
300 Radiation element (diaphragm, coil)
400 Gas molecule, condensate

What is claimed is:
1. A device for determining a concentration of a gas component in an inhaled gas or in an exhaled gas of a living being, the device comprising:
 a radiation source configured to emit light or heat radiation in a radiation direction in a wavelength range of lambda1 ($\lambda$1)=2.5 µm to lambda2 ($\lambda$2)=14.0 µm, wherein the radiation source is configured as:
  a flat radiator, as a diaphragm radiator or as a radiation element and is configured with an essentially planarly configured radiating surface; or a light-emitting diode (LED) configured with an essentially planarly configured radiating surface; and
the radiating surface is configured for mainly uniform radiation over the radiating surface;
a detector array with at least two detector elements configured to detect the radiation generated by the radiation source;
at least two bandpass filter elements each of the filter elements being arranged at one of the at least two detector elements;
at least one optically reflecting element having a flat configuration and arranged opposite the radiation source; and
a control unit configured to control operation of the radiation source and to detect the signal of the at least two detector elements, wherein:
at least one of the at least two bandpass filter elements is configured to be optically transparent for infrared radiation which is absorbed by a measured gas;
at least one of the at least two bandpass filter elements is configured to be optically transparent for a radiation that is not absorbed by the measured gas;
at least one of the two detector elements with at least one of the bandpass filter elements is arranged in an angular arrangement at an angle in a range of 20° to 80° in relation to an axis extending through the radiation source parallel to or identical to the radiation direction of the emission of the radiation source;
the radiating surface is perpendicular to the axis;
the radiating surface comprises an area in a range of 2.0 mm² to 10 mm²;
each of the at least two detector elements is arranged at a first distance from the axis in a range of 0.1 mm to 10.0 mm;
each of the at least two bandpass filter elements is arranged at a second distance from the axis in a range of 0.1 mm to 10.0 mm;
the detector array is arranged on a same side, with respect to the oppositely arranged reflecting element, as the radiation source and is arranged adjacent to the radiation source;
the at least two detector elements are arranged at a reflecting element distance from the reflecting element in a range of 0.1 mm to 5.0 mm; and
the reflecting element distance is a distance directly in a range of or along the axis extending from the reflecting element between the at least two detector elements.

2. A device in accordance with claim 1, wherein:
the detector array is arranged opposite the radiation source at a detector array to source distance in a range of 0.1 mm to 10.0 mm;
the detector array to source distance is obtained as a distance directly in a range of or along the axis extending between the two detector elements;
the radiation source is arranged centrally on the axis extending between the two detector elements.

3. A device in accordance claim 1, wherein the bandpass filter elements are configured to optical filter infrared light in a transmission range of a wavelength range of 2.5 µm to 14 µm.

4. A device in accordance with claim 1, wherein the detector elements are configured as pyrodetectors, bolometers, semiconductor detectors, thermopiles or thermocouples.

5. A device in accordance with claim 1, wherein:
at least two other of the at least two detector elements, with at least one of the bandpass filter elements, is arranged in an angular arrangement at an angle in a range of 20° to 80° in relation to the axis extending through the radiation source parallel to or identical to radiation direction of the emission of the radiation source to provide the detector array with more than two angular arrangements with detector elements and with bandpass filter elements in a spatial arrangement in the form of lateral surfaces of a rectangular or square truncated pyramid around a center.

6. A device in accordance with claim 1, wherein the detector array forms, together with the radiation source, a flow guide element configured to guide inhaled gas and/or exhaled gas, so that the measured gas flows through the flow guide element as a main stream and the gas concentration can be detected in the main stream.

7. A device in accordance with claim 1, wherein:
the detector array is configured together with the radiation source as a component of a flow guide element;
the flow guide element is configured to guide inhaled gas and/or exhaled gas such that the measured gas used for the concentration measurement is the measured gas that is representative of quantities of gas that flows through the component essentially in a center of the flow guide element as a side stream as a part of a main stream; and
a concentration measurement in the measured gas is detectable in the side stream.

8. A device in accordance with claim 1, wherein
the detector array together with the radiation source is configured as a component arranged laterally in a flow guide element;
the flow guide element is configured for guiding inhaled gas and/or exhaled gas such that the measured gas used for the concentration measurement is measured gas that is representative of quantities of gas that flows through the component essentially in a lateral edge area of the flow guide element in a side stream as part of a main stream; and
a concentration measurement in the measured gas is detectable in the side stream.

* * * * *